US00PP33383P2

(12) United States Plant Patent
Leslie et al.

(10) Patent No.: US PP33,383 P2
(45) Date of Patent: Aug. 24, 2021

(54) WALNUT TREE NAMES 'WOLFSKILL'

(50) Latin Name: *Juglans regia*
Varietal Denomination: UC Wolfskill

(71) Applicant: The Regents of the University of California, Oakland, CA (US)

(72) Inventors: Charles A. Leslie, Davis, CA (US); Gale H. McGranahan, Davis, CA (US); Patrick J. Brown, Davis, CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 16/949,746

(22) Filed: Nov. 12, 2020

(51) Int. Cl.
*A01H 5/00* (2018.01)
*A01H 6/00* (2018.01)

(52) U.S. Cl.
USPC ..... Plt./154
CPC ..... *A01H 6/00* (2018.05)

(58) Field of Classification Search
USPC ..... Plt./154
CPC ..... A01H 5/08; A01H 5/00
See application file for complete search history.

(56) References Cited

U.S. PATENT DOCUMENTS

PP4,388 P 2/1979 Forde
PP25,466 P3 4/2015 McGranahan et al.

*Primary Examiner* — Kent L Bell
(74) *Attorney, Agent, or Firm* — McKee, Voorhees & Sease, PLC

(57) ABSTRACT

A new walnut variety (*Juglans regia*) designated as 'UC Wolfskill' is provided. This variety has a harvest date 10 days earlier than walnut variety 'Chandler' and produces a walnut that is jumbo in size with light colored kernels.

10 Drawing Sheets

Latin name: Botanical/commercial classification: *Juglans regia*, new English walnut tree cultivar.

Tree denomination: The variety denomination of the claimed walnut variety is 'UC Wolfskill'.

BACKGROUND OF INVENTION

It has long been recognized as desirable to provide walnut trees bearing large crops that are ripe for commercial harvesting and shipment early in the harvest season. In particular, the California walnut industry is in need of earlier harvesting walnut varieties, as the most commonly planted variety 'Chandler' (U.S. Plant Pat. No. 4,388) harvests late in the season (early to mid-October), which delays processing. Further, the walnut industry desires walnut cultivars with light kernel color for marketing value. Thus, there exists a need for improved walnut varieties with mid-season harvest dates and desirable walnut characteristics. The tree of the present cultivar, 'UC Wolfskill', produces a nut that has high quality but is ready for harvest approximately 10 days before 'Chandler', about the same time as the reference cultivar 'Solano' (U.S. Plant Pat. No. 25,466).

BRIEF SUMMARY OF THE INVENTION

The present invention relates to a new and distinct cultivar of walnut tree (*Juglans regia*) that has been denominated as 'UC Wolfskill' and more particularly to a walnut tree that has a harvest date 10 days earlier than the walnut tree cultivar 'Chandler' and that further produces a walnut that is jumbo in size with light colored kernels.

It was found that the new *Juglans regia* cultivar of the present invention exhibits the following combination of characteristics:

a) forms jumbo-sized walnuts that possess extra light-colored kernels;
b) bears well-filled nuts with shells that are light colored, relatively thin, and attractive in appearance;
c) bears fruit both terminally and laterally;
d) yields a crop that can be harvested approximately 10 days before 'Chandler'; and
e) is protandrous, bearing male flowers before female flowers.

The new *Juglans regia* walnut tree of the present invention was created at Davis, Calif. in Year 1 by a controlled pollination between 'Chandler' and 'Solano'. The breeding pedigree is shown in FIG. 1.

Seeds from the cross were planted and the resulting 5282 trees were carefully observed along with other trees in the walnut breeding program. When they began to bear nuts, data were collected annually on leafing date, first, peak and last female flower bloom, first, peak and last male bloom, blight severity and yield. Nuts were sampled, cracked, and data was collected on shell appearance, shell thickness, shell integrity, shell strength, nut weight, kernel weight, percent kernel, ease of kernel removal, kernel color, and percent kernel shrivel. A single tree was selected from among progeny of this controlled cross based on its superior attributes. This selection was originally designated 'UC03-001-2357' and is now designated the 'UC Wolfskill' cultivar after John R. Wolfskill, an early pioneer in California horticulture. Compared to 'UC Wolfskill', the male parent 'Solano' has similar phenology but fewer extra light kernels; the female parent 'Chandler' is later harvesting than 'UC Wolfskill' and nuts have a lower percent kernel fill (TABLE 2).

The new cultivar of the present invention has been asexually propagated by grafting on 'Paradox' rootstock in selection blocks at Davis and in grower field trials at Woodland, Durham, Wheatland, Red Bluff, Rio Oso, Merced, and Crow's Landing Calif., and at major California walnut nurseries. The distinctive characteristics of the new cultivar have been found to be stable and are transmitted to the new trees when asexually propagated.

BRIEF DESCRIPTION OF THE TABLES

TABLE 1 shows trial locations, number of trees at each site, and number of years of data collected at each location.

TABLE 2 shows summarized phenology, tree, and nut evaluations for 'UC Wolfskill', both parents, and several comparison cultivars.

TABLE 3 shows a key to evaluation traits presented in TABLE 2.

DETAILED BOTANICAL DESCRIPTION

The description is based on an ungrafted walnut tree on its own roots and trees subsequently grafted on 'Paradox' rootstock growing in selection blocks at Davis, and grower trials near Woodland, Durham, Merced, Wheatland, and Rio Oso, Calif. Data were collected on the own rooted tree from Year 5 (age 3 years) to Year 15 (age 13 years). Data from Year 9 to Year 17 were collected from grafted trees. The Munsell Color Charts for Plant Tissues (GretagMacbeth LLC, 617 Little Britain Road, New Windsor, N.Y. 12553-6148) is used in the identification of color. Also, common color terms are to be accorded their ordinary dictionary significance.

Botanical classification: *Juglans regia*

Female parent: 'Chandler'

Male parent: 'Solano'.

Figure 1:
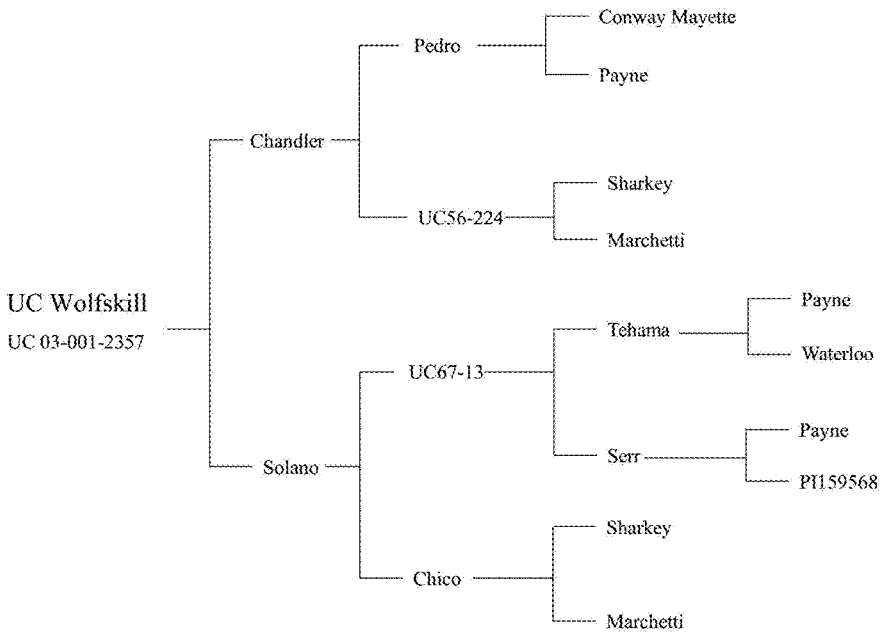
FIG. 1 shows the breeding pedigree of the 'UC Wolfskill' walnut.
Figure 2:
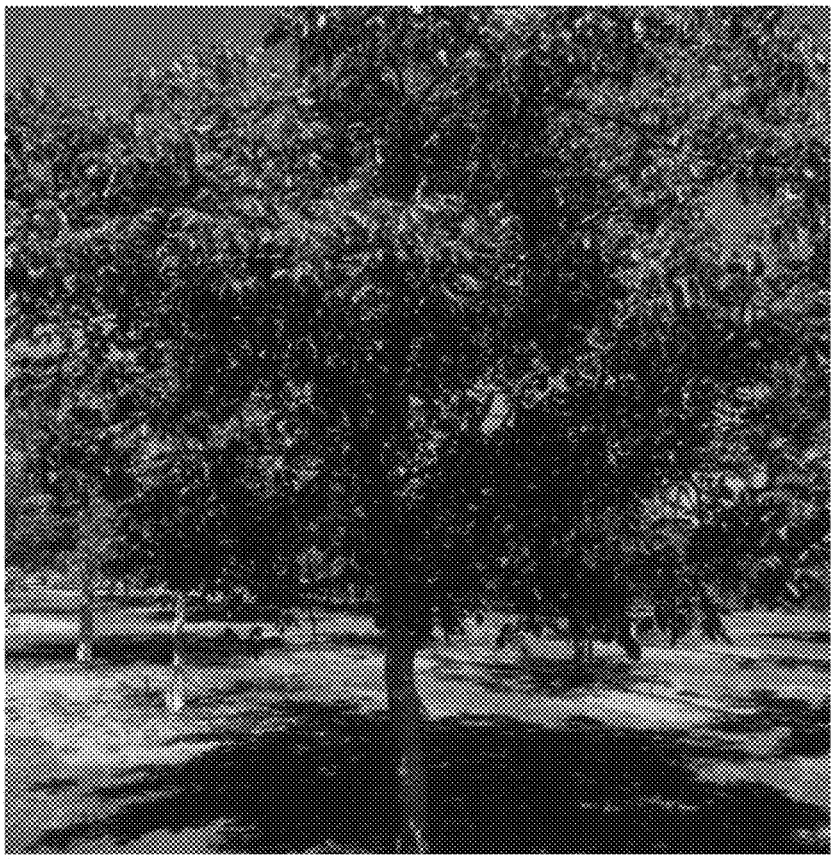
FIG. 2 shows a tree of 'UC Wolfskill' walnut at 7 years.
Figure 3:
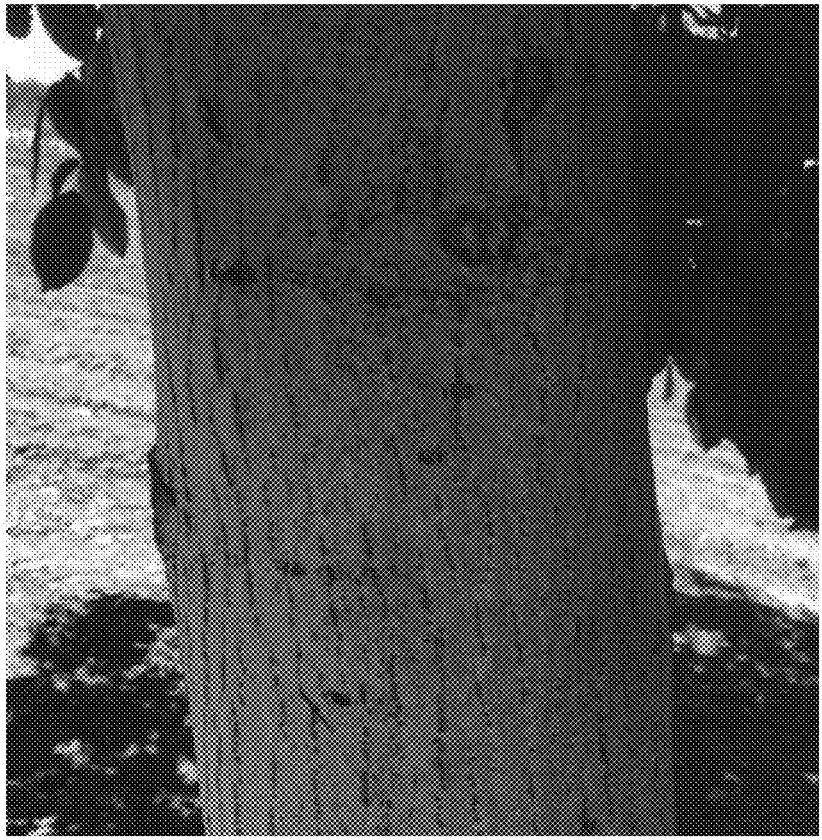
FIG. 3 shows bark of 'UC Wolfskill' walnut.

Plant: The growth habit of the plant is illustrated in FIG. 2. This 7 year old tree is approximately 6.85 meters in height with a canopy diameter of 6.2 meters. The trunk diameter at 0.5 meters above the ground is approximately 19 cm. The silvery grey bark is typical of *Juglans regia*. The young bark is brown (5Y 7/2) and the older bark is grey (2.5Y 8/2) with raised lighter lenticels (5YR 8/2) (FIG. 3). Lenticels are round to oval in shape, 1-5 mm×1-2 mm in size. 'UC Wolfskill' has vigor similar to 'Chandler'.

Figure 4:
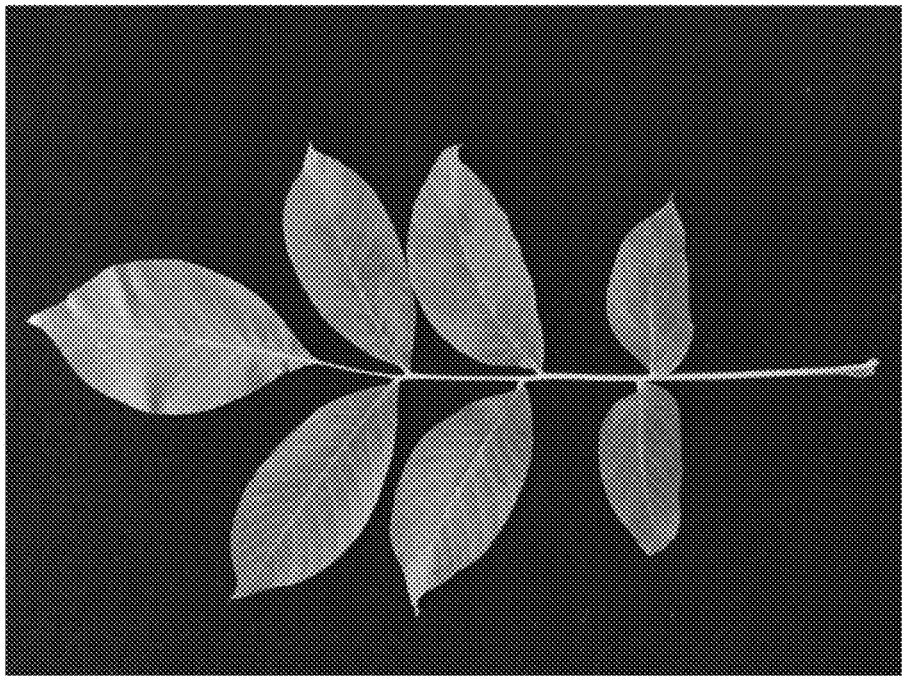
FIG. 4 shows adaxial view of leaf of 'UC Wolfskill' walnut.
Figure 5:
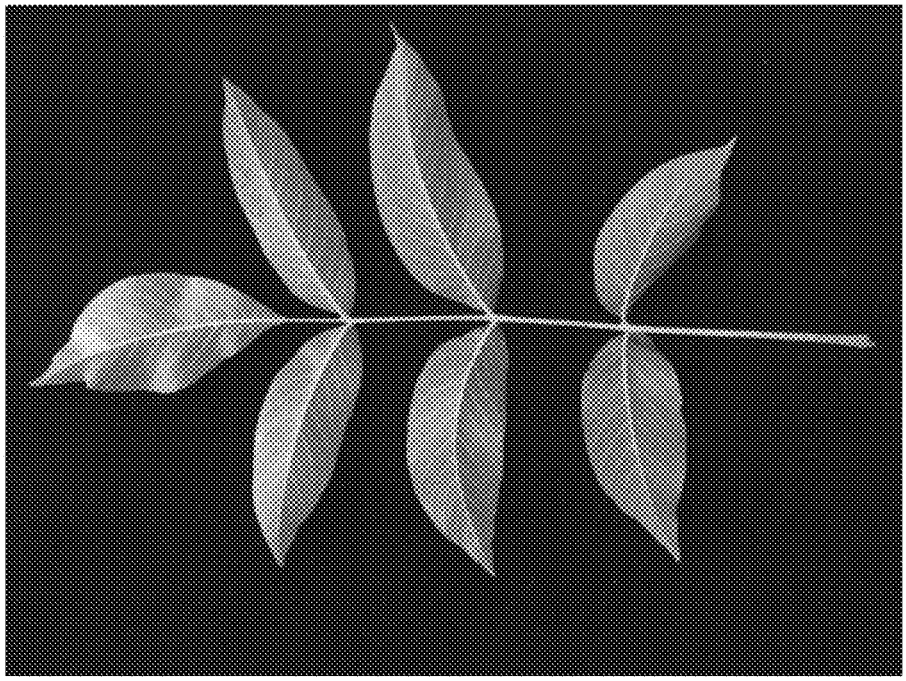
FIG. 5 shows abaxial view of leaf of 'UC Wolfskill' walnut.

Foliage: The dark green foliage is illustrated in FIG. 4 and FIG. 5 and is typical of *Juglans regia*. Leafing out date between Year 6 and Year 17 has occurred on March 27$^{th}$ on the average. For comparative purposes, the 'Chandler' cultivar leaf-out is April 5$^{th}$. The typical leaf coloration is green (adaxial 7.5GY 4/4, abaxial 5GY 5/2). The leaves are pinnately compound with 7-9 leaflets. The full leaf length is approximately 39 cm. and width is 27 cm. Leaflets are broadly elliptical and entire. The terminal leaflet averages 17 cm in length and 8 cm in width. The middle leaflets average 13 cm in length and 6 cm in width and the proximal leaflets average 8 cm in length and 4 cm in width. The rachis averages 30 cm in length and 2-4 mm in diameter. Petiole length is 10 cm and is 2.5GY 8/8 in color.

Figure 6:
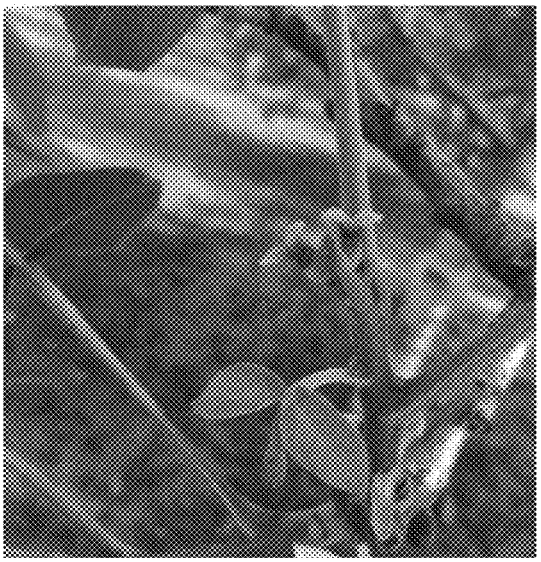
FIG. 6 shows female flowers of 'UC Wolfskill' walnut.
Figure 7:
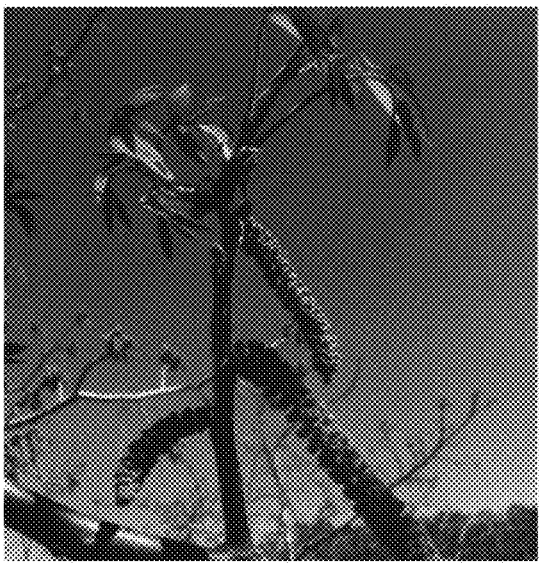
FIG. 7 shows catkins (male flowers) of 'UC Wolfskill' walnut

Inflorescence: The tree is precocious with first yield being noted at age 3 years. Male flowers (catkins) were first present at age 4 years. This delay in male maturity is typical of *Juglans regia*. From Year 6 to Year 17, average first female bloom occurred on April 11, peak bloom on April 14 and last bloom on April 18. From Year 6 to Year 17, average male flowering (pollen shedding) began March 28, peaked on April 4 and terminated April 10. Pollen shedding in this protandrous variety does not cover pistillate bloom well, suggesting that a pollinizer could be helpful for maximum yield. 'Chandler', 'Howard' (U.S. Plant Pat. No. 4,405), or 'Tulare' (U.S. Plant Pat. No. 8,268) would be satisfactory pollinizers. The female flowers are typical of *Juglans regia* (FIG. 6) with two flowers per inflorescence borne on 1 cm spikes at both terminal and lateral positions on current season's growth. Approximately 97% of the lateral buds contain inflorescences, making yields much greater than trees that only bear flowers terminally. A typical female flower is approximately 8 to 10 mm at anthesis and floral organs are typical of *J. regia*. The flowers appear vase-shaped when the 2 plumose stigmatic arms are curved outward. There are no petals. The female flowers are green (5GY 7/8) in color. The flower fragrance is typical of *J. regia* and is not noticeably different from the foliage fragrance. The male flowers (FIG. 7) are borne on catkins, between 7 and 14 cm in length and 1-2 cm in diameter, and are green in color (5GY 7/10).

Figure 8:
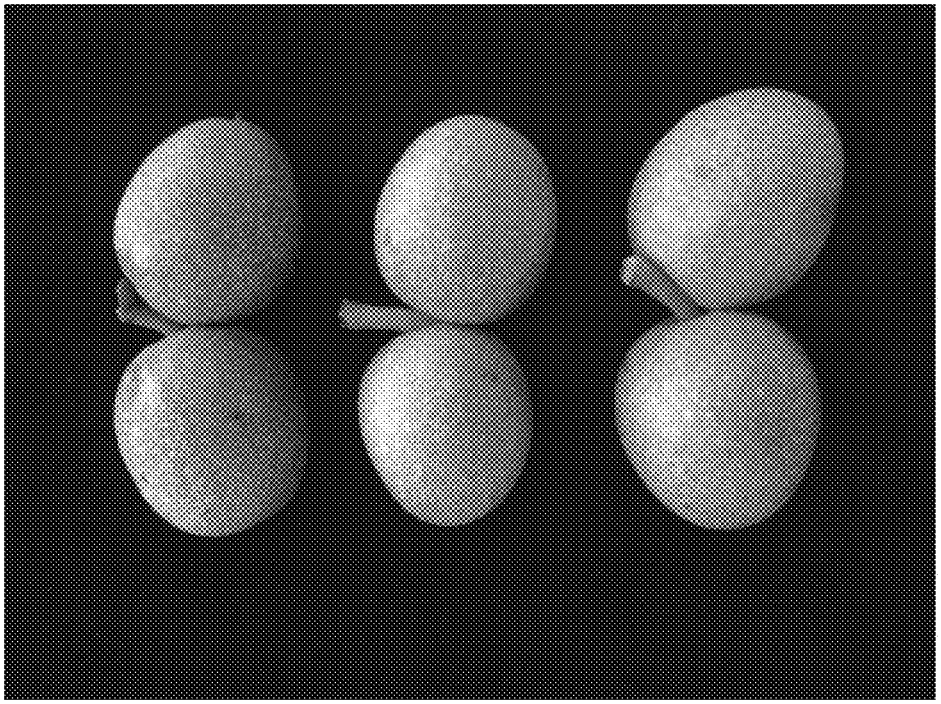
FIG. 8 shows hulls of 'UC Wolfskill' walnut.
Figure 9:
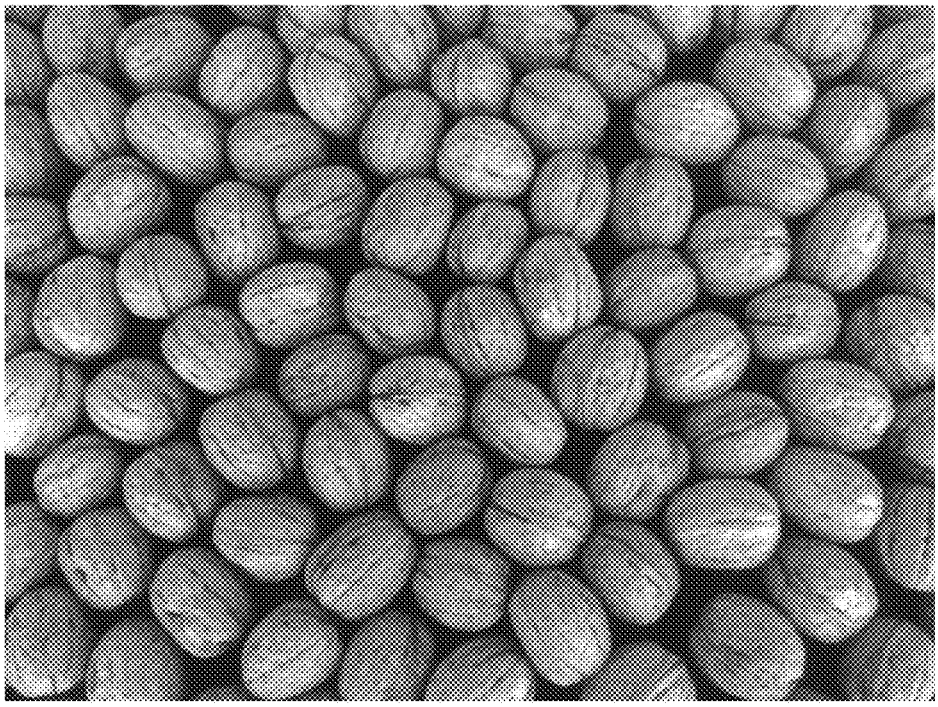
FIG. 9 shows nuts of 'UC Wolfskill' walnut.
Figure 10A:
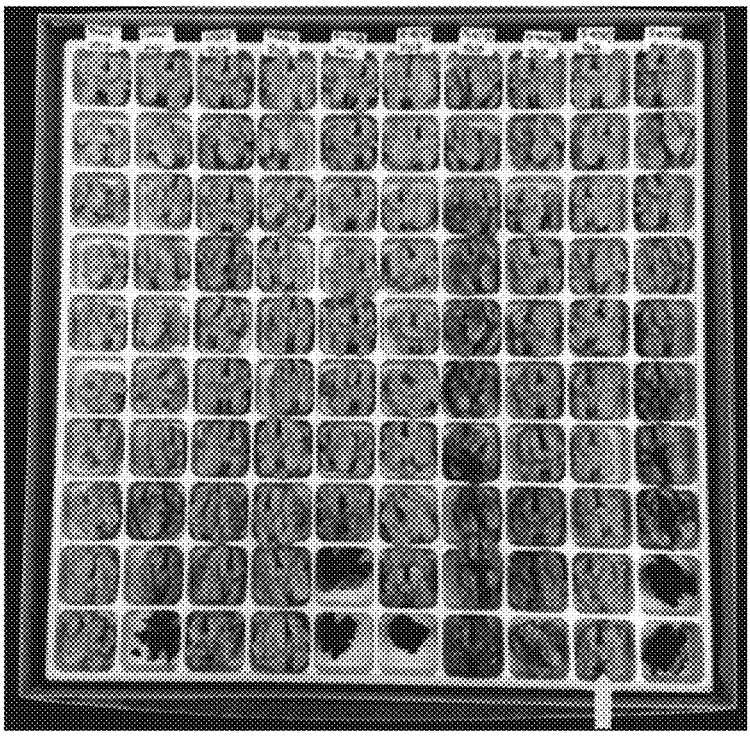
FIG. 10A shows a comparison of the kernels of 'UC Wolfskill' walnut to other walnut cultivars (the kernels of 'UC Wolfskill' is shown in the column indicated by the arrow).
Figure 10B:
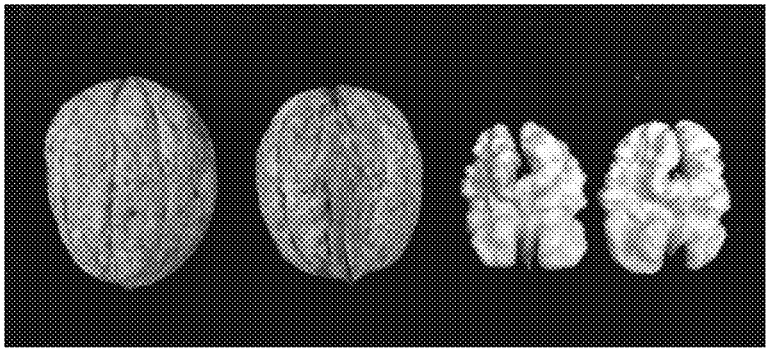
FIG. 10B shows nuts and kernels of 'UC Wolfskill' walnut.

Walnuts: The new cultivar commonly harvests about 10 days before 'Chandler', about 13 days after 'Payne' (unpatented), and is similar in timing to 'Solano'. The new cultivar has excellent yields of mostly jumbo-sized walnuts. The hull is broadly elliptic, 5.1 cm×4.6 cm, 7 mm thick, and 7.5GY 7/4 in color with numerous lighter speckles (FIG. 8). The nut is broadly ovate, has a lightly grooved shell, is a light tan color (7.5YR 6/4) and measures approximately 40 mm in length and 34 mm in width (FIG. 9). The shell is 1.2 mm thick, average strength and well-sealed, and the kernel is easy to remove. The kernel weight averages 8.1 g and makes up 58% of the total nut weight of 14.1 g. Kernel color is considered excellent (FIG. 10) and scores mostly in the light to extra light categories (i.e.; 33% extra light, 57.4% light, 9.8% light amber, and 0% amber) of the USDA Standards for Grades of Shelled Walnuts as determined by using the standard Walnut Color Chart for kernels published by the Dried Fruit Association of California (TABLE 2). In addition, kernels of 'UC Wolfskill' have averaged 57.1 on the Relative Light Index used by Diamond Foods of Stockton, Calif. It is typical of commercial walnuts in terms of flavor and firmness.

Disease susceptibility: This cultivar appears have somewhat lower incidence of blight (*Xanthomonas arboricola* pv. *juglandis*) than other cultivars with comparable leafing dates.

Usage: This new cultivar of the present invention provides a mid-season walnut with high quality light-colored kernels, harvesting earlier than 'Chandler' with greater kernel fill and similar kernel color and shell traits.

TABLE 1

Trial sites, locations, number of trees at location, and years of evaluation data collected for 'UC Wolfskill'.

| | Location | Year Planted | # Trees Evaluated | # Years of Data Collected | Comparison Cultivars Evaluated at Same Location |
|---|---|---|---|---|---|
| Trial Site | | | | | |
| UC Davis - North Seedling Block | Davis | Year 3 | 1 | 11 | Chandler, Solano, Durham (U.S. Plant Pat. No. 28,529), Tulare, Vina, Howard, Ivanhoe |
| UCD Selection Block D | Davis | Year 8 | 4 | 8 | Chandler, Solano, Durham, Tulare, Vina, Howard, Ivanhoe |
| Scheuring S505 C | Woodland | Year 8 | 4 | 9 | Chandler, Solano, Durham, Tulare, Vina, Howard, Ivanhoe |
| Stolp D | Durham | Year 8 | 4 | 8 | Chandler, Solano, Durham, Tulare, Howard, Ivanhoe |
| Whitney Warren Ranch A | Wheatland | Year 8 | 4 | 6 | Chandler, Solano, Howard, Tulare, Hartley, Vina, |
| Norene B | Rio Oso | Year 12 | 20 | 4 | Chandler, Solano, Durham, 03-001-1372 |
| Crane | Merced | Year 12 | 11 | 2 | Chandler, Solano, Durham, Tulare, 03-001-1938, 03-001-1457, 06-005-31 |
| Gilbert B | Wheatland | Year 14 | 55 | 3 | Chandler, Solano, Dur-ham, 03-001-1938, 03-001-1372, 03-001-2440, 06-005-31 |
| Orestimba Nursery | Crow's Landing | Year 14 | ~50 | observational | Chandler, Solano, Tulare, 03-001-1372, 03-001-1938, 03-001-2440, 00-006-227 |
| Norene C | Rio Oso | Year 17 | ~500 | new | Chandler, Solano, Durham, Tulare, Howard, Vina, 03-001-1372 |
| Nursery Locations | | | | | |
| Sierra Gold Nursery | Yuba City | Year 14 | | nursery | for increase |
| Burchell Nursery | Oakdale | Year 14 | | nursery | for increase |
| Dave Wilson Nursery | Hughson | Year 15 | | nursery | for increase |

TABLE 1-continued

Trial sites, locations, number of trees at location, and years of evaluation data collected for 'UC Wolfskill'.

| | Location | Year Planted | # Trees Evaluated | # Years of Data Collected | Comparison Cultivars Evaluated at Same Location |
|---|---|---|---|---|---|
| Venice Hills Nursery | Visalia | Year 18 | | nursery | for increase |

TABLE 2

Performance of 'UC Wolfskill' compared to its parents and similar cultivars - means and standard errors for all locations Year 5 to Year 17.

| Trait (units) | Year-locations evaluated | UWolfskill | Chandler | Solano |
|---|---|---|---|---|
| Leafing date (days) | 14 | 3/26 ± 1.5 | 4/6 ± 1.6 | 3/25 ± 1.5 |
| Pollen shed date (days) | 13 | 4/4 ± 1.7 | 4/13 ± 1.3 | 4/3 ± 1.3 |
| Female bloom date (days) | 13 | 4/14 ± 1.7 | 4/22 ± 1.1 | 4/11 ± 1.3 |
| Harvest date (days) | 17 | 9/26 ± 1.7 | 10/6 ± 1.1 | 9/20 ± 1.9 |
| Yield (0-9 scale) | 19 | 7.3 ± 0.1 | 6.5 ± 0.1 | 7.2 ± 0.1 |
| Blight (0-9 scale) | 13 | 1.1 ± 0.5 | 0.9 ± 0.3 | 2.4 ± 0.5 |
| Inshell weight (g) | 34 | 14.0 ± 0.2 | 12.9 ± 0.3 | 14.7 ± 0.3 |
| Kernel weight (g) | 34 | 8.2 ± 0.2 | 6.4 ± 0.2 | 8.0 ± 0.2 |
| Percent kernel (%) | 34 | 58.4 ± 0.5 | 50.0 ± 0.5 | 54.5 ± 0.4 |
| Ease of removal (0-9 scale) | 34 | 4.5 ± 0.1 | 3.8 ± 0.1 | 4.5 ± 0.1 |
| Percent extra light (%) | 34 | 68 ± 5 | 70 ± 5 | 50 ± 6 |
| Percent light (%) | 34 | 30 ± 4 | 25 ± 4 | 46 ± 6 |
| Percent light amber (%) | 34 | 1 ± 1 | 5 ± 2 | 4 ± 2 |
| Percent tip shrivel (%) | 34 | 4 ± 1 | 28 ± 3 | 8 ± 3 |

| Trait (units) | Vina (not patented) | Howard | Tulare | Durham U.S. Plant Pat. No. 28,529 |
|---|---|---|---|---|
| Leafing date (days) | 3/27 ± 1.7 | 4/6 ± 28,529 | 4/3 ± 1.9 | 3/30 ± 1.9 |
| Pollen shed date (days) | 4/5 ± 1.5 | 4/10 ± 1.5 | 4/12 ± 1.6 | 4/6 ± 1.4 |
| Female bloom date (days) | 4/12 ± 1.4 | 4/20 ± 1.3 | 4/17 ± 1.5 | 4/16 ± 1.4 |
| Harvest date (days) | 9/22 ± 1.2 | 9/27 ± 1.4 | 9/28 ± 1.7 | 9/24 ± 1.0 |
| Yield (0-9 scale) | 7.1 ± 0.1 | 6.9 ± 0.1 | 7.3 ± 0.1 | 6.6 ± 0.2 |
| Blight (0-9 scale) | 3.9 ± 0.6 | 0.6 ± 0.3 | 1.6 ± 0.7 | 0.2 ± 0.2 |
| Inshell weight (g) | 13.9 ± 0.5 | 13.4 ± 0.4 | 13.9 ± 0.4 | 15.1 ± 0.2 |

TABLE 2-continued

Performance of 'UC Wolfskill' compared to its parents and similar cultivars - means and standard errors for all locations Year 5 to Year 17.

| | | | | |
|---|---|---|---|---|
| Kernel weight (g) | 7.0 ± 0.3 | 6.8 ± 0.2 | 7.6 ± 0.2 | 8.4 ± 0.2 |
| Percent kernel (%) | 50.4 ± 0.5 | 50.9 ± 0.3 | 54.2 ± 0.5 | 55.3 ± 0.4 |
| Ease of removal (0-9 scale) | 5.1 ± 0.1 | 4.6 ± 0.1 | 4.5± 0.1 | 4.2 ± 0.1 |
| Percent extra light (%) | 1 ± 1 | 16 ± 4 | 6 ± 3 | 47 ± 6 |
| Percent light (%) | 42 ± 9 | 69 ± 5 | 80 ± 4 | 49 ± 6 |
| Percent light amber (%) | 56 ± 9 | 15 ± 4 | 13 ± 4 | 3 ± 1 |
| Percent tip shrivel (%) | 0 ± 0 | 3 ± 1 | 8 ± 2 | 19 ± 4 |

TABLE 3

Key to evaluation traits presented in TABLE 2.

| | |
|---|---|
| Tree evaluation | |
| Catkin abundance | Male flower abundance: 3 low; 5 intermediate; 7 high |
| Female abundance | Female flower abundance: 3 low; 5 intermediate; 7 high |

TABLE 3-continued

Key to evaluation traits presented in TABLE 2.

| | |
|---|---|
| Lateral fruitfulness % | Percent of lateral buds with female flowers |
| Yield | Yield: 3 low; 5 intermediate; 7 high |
| Nut and kernel traits | |
| Texture | Shell texture: 3 smooth; 5 medium; 7 rough |
| Color | Shell color: 3 light; 5 medium; 7 dark |
| Seal | Shell seal: 3 weak; 5 intermediate; 7 strong |
| Strength | Shell strength: 3 weak; 5 intermediate; 7 strong |
| Integrity | Shell integrity: 3 substantial area of shell missing; 5 small area of missing shell; 6 stem end hole; 7 complete shell |
| Thickness | Shell thickness at mid-cheek in mm |
| Packing tissue | Inner lining: 3 thin; 5 medium; 7 thick |
| Inshell weight | g |
| Kernel weight | g |
| Kernel % | Kernel wt/inshell wt × 100 |
| Fill | Kernel fill: 3 poor; 5 moderate; 7 well |
| Plumpness | Kernel plumpness: 3 thin; 5 moderate; 7 plump |
| Ease of removal | Ease of removal of kernel halves: 3 easy; 5 moderate; 7 difficult |
| Blanks % | Percent of nuts without a kernel |
| Extra light % | Percent of kernels in extra light category (DFA*) |
| Light % | Percent of kernels in light category (DFA) |
| Light amber % | Percent of kernels in light amber category (DFA) |
| Amber % | Percent of kernels in amber category (DFA) |
| Tip shrivel % | Percent of kernels with tip shrivel like Chandler |
| <50% shrivel | Percent of kernels with <50% shrivel |
| >50% shrivel | Percent of kernels with >50% shrivel |
| Veins % | Percent of kernels with conspicuous veins |

*"DFA" refers to Dried Fruit Association of CA

What is claimed is:

1. A new and distinct variety of walnut tree designated 'UC Wolfskill' as shown and described herein.

* * * * *